United States Patent
Quittner (10) Patent No.: US 12,144,931 B2
(45) Date of Patent: Nov. 19, 2024

(54) SYSTEM AND METHOD FOR PRODUCING SOUND AND LIGHT FOR THERAPEUTIC EFFECT

(71) Applicant: Katherine Quittner, Shelburne, VT (US)

(72) Inventor: Katherine Quittner, Shelburne, VT (US)

(*) Notice: Subject to any disclaimer, the term of this patent is extended or adjusted under 35 U.S.C. 154(b) by 0 days.

(21) Appl. No.: 18/597,307

(22) Filed: Mar. 6, 2024

(65) Prior Publication Data

US 2024/0269424 A1 Aug. 15, 2024

Related U.S. Application Data

(63) Continuation of application No. PCT/US2023/076577, filed on Oct. 11, 2023.

(60) Provisional application No. 63/379,046, filed on Oct. 11, 2022.

(51) Int. Cl.
*A61M 21/00* (2006.01)

(52) U.S. Cl.
CPC ..... *A61M 21/00* (2013.01); *A61M 2021/0027* (2013.01); *A61M 2021/005* (2013.01)

(58) Field of Classification Search
None
See application file for complete search history.

(56) References Cited

U.S. PATENT DOCUMENTS

| | | | |
|---|---|---|---|
| 9,685,149 B2 | 6/2017 | Quittner | |
| 10,068,560 B1 | 9/2018 | Quittner | |
| 11,141,604 B2 | 10/2021 | Malchano et al. | |
| 11,517,709 B1* | 12/2022 | Fung | G06F 3/016 |
| 2017/0143934 A1* | 5/2017 | Tsai | A61H 23/00 |
| 2018/0133504 A1 | 5/2018 | Malchano et al. | |
| 2020/0139078 A1 | 5/2020 | Noftsker | |
| 2020/0398021 A1 | 12/2020 | Garza et al. | |
| 2022/0212030 A1 | 7/2022 | Vyshedskiy | |
| 2022/0406271 A1 | 12/2022 | Chen et al. | |

FOREIGN PATENT DOCUMENTS

| | | |
|---|---|---|
| CN | 114995938 A | 9/2022 |
| WO | 2022027030 A1 | 2/2022 |

OTHER PUBLICATIONS

Ann-Katrin Becher, et al., "Intracranial electroencephalography power and phase synchronization changes during monaural and binaural beat stimulation" (abstract only), Eur. J. Neuroscience 41:254 (2015).

Nantawachara Jirakittayakorn, et al., "Brain Responses to 40-Hz binaural beats and effects on emotion and memory" (abstract only), Int. J. Psychophysiology 120:96 (2017).

(Continued)

*Primary Examiner* — Thaddeus B Cox
(74) *Attorney, Agent, or Firm* — Ice Miller LLP (57) ABSTRACT

A method for providing therapeutic light and sound, the method includes presenting, on a computing device, a musical composition including a substantially continuous tone having a specified audible first frequency embedded therein; presenting, on the computing device, a visual display including light having a visually perceived specified second frequency; and determining, via facial recognition, that an identified user is in a proximity of musical composition and the visual display being presented.

5 Claims, 5 Drawing Sheets

(56) References Cited

OTHER PUBLICATIONS

Anne Trafton, "Why visual stimulation may work against Alzheimer's", MIT News, May 7, 2019.
David Orenstein, "Small studies of 40-hertz sensory stimulation confirm safety, suggest Alzheimer's benefits", MIT News, Dec. 13, 2022.
David Orenstein, "40 Hz vibrations reduce Alzheimer's pathology, symptons in mouse models", MIT News, Jun. 5, 2023.
International Patent Application No. PCT/US2023/076577, International Search Report, Written Opinion of the International Searching Authority (Feb. 5, 2024).

* cited by examiner

SYSTEM AND METHOD FOR PRODUCING SOUND AND LIGHT FOR THERAPEUTIC EFFECT

This application is a continuation application of International Application No. PCT/US23/76577, filed Oct. 11, 2023, which claims the benefit of U.S. Provisional Application No. 63/379,046, filed Oct. 11, 2022, which are hereby incorporated by reference herein in their entirety.

BACKGROUND

Unless otherwise indicated herein, the materials described in this section are not prior art to the claims in this application and are not admitted to being prior art by inclusion in this section.

Dementia (vascular dementia and Alzheimer's disease) affects about 50 million people worldwide, with 10 million new cases occurring every year. Symptoms and pathology of Alzheimer's disease include the formation of neurofibrillary tangles inside their neurons—dysfunctional knots of a protein called tau—that can lead to the cell's death, and amyloid beta plaques—sticky heaps of protein—that dam the flow of communication between neurons. Bathing patients in flashing light and pulsing sounds both tuned to a frequency of 40 hertz may reverse signs of Alzheimer's disease in the brain.

Brain waves are generated when large groups of neurons oscillate on and off together. Neurons encode thoughts and actions and senses in these oscillations. Brain waves known as "gamma" brain waves help connect and process information throughout the brain. These gamma brain waves are diminished in Alzheimer's disease. Exposure to light to flashing at 40 hertz and sound reproduced at 40 hertz can cause the brain to generate gamma waves at a corresponding 40 hertz and may provide a therapeutic effect of reducing the amyloid plaques and tau tangles. By providing the brains with a regular beat, the repeating light and sound may work as a kind of metronome for brain activity.

Dementia-afflicted patients can have difficulty focusing and following and complying with therapeutic instructions or requirements. These attributes can make delivery of therapies such as the light and sound therapies discussed herein challenging because the therapeutic effect is believed to increase with sustained exposure of the 40 Hz light and sound signals through the patient's eyes and ears, but if interrupted or only briefly administered, the therapeutic effect is diminished or, at bottom, ineffective (except for causing frustration and anxiety in the patient). Therapies that involve donning headphones, ear pieces, glasses or goggles, or similar devices typically are met with hostility by patients and are generally not tolerated for sufficient periods of time to deliver the therapeutic signals effectively. Dementia-afflicted patients are notoriously uncooperative and non-compliant especially with unexpected deviations in their habitual routines or with attempts to force the patient to participate in an activity that appears mysterious or unfamiliar to them.

On the other hand, dementia-afflicted patients are known to respond well to certain familiar songs and other sound therapies, such as those described in U.S. Pat. Nos. 9,685,149 and 10,068,560 by the same inventor as named in the present disclosure. A need exists, therefore, among others, for a therapy that can administer a 40 Hz signal through a patient's eyes and ears simultaneously while displaying on a video screen a therapeutic video augmented by a 40 Hz therapeutic visual signal and playing on a speaker a therapeutic sound augmented by a 40 Hz therapeutic sound signal without requiring the patient to don or wear any device or attach any device to the patient.

SUMMARY

Apparatuses and methods for providing sound and light for producing therapeutic effects are provided.

According to various aspects there is provided a method for providing sound and light for producing therapeutic effects. In some aspects, the method may include presenting, on a computing device, a musical composition including a substantially continuous tone having a specified audible first frequency embedded therein; presenting, on the computing device, a visual display including light having a visually perceived specified second frequency; and determining, via facial recognition, that an identified user is in a proximity of musical composition and the visual display being presented.

According to various aspects there is provided a computing device for providing sound and light for producing therapeutic effects. In some aspects, the computing device may include video circuitry including a video display; audio circuitry including an audio output transducer; and a processor configured to communicate with the video display and the audio circuitry. The processor further configured to cause the audio circuitry to present, via the audio output transducer, a musical composition including a substantially continuous tone having a specified audible first frequency embedded therein; cause the video circuitry to present, via the video display, a visual display including light having a visually perceived specified second frequency; and execute a facial recognition routine to determine that the identified user is in a proximity of musical composition and the visual display being presented.

According to various aspects there is provided a non-transitory computer readable medium. In some aspects, the non-transitory computer readable medium may include instructions for causing one or more processors to perform operations for providing sound and light for producing therapeutic effects. The operations may include presenting, on a computing device, a musical composition including a substantially continuous tone having a specified audible first frequency embedded therein; presenting, on the computing device, a visual display including light having a visually perceived specified second frequency; and determining, via facial recognition, that an identified user is in a proximity of musical composition and the visual display being presented.

According to various aspects there is provided a method for presenting a therapeutic light on a computing device that includes a display screen. The method comprises presenting on the display screen a visual display comprising first and second images. The first image is presented in a first portion of the visual display. The second image is presented in a second portion of the visual display positioned at the perimeter of the first portion. The first image is selected from the group consisting of: a graphic image, a sequence of graphic images, a video image, and an interactive video image. The second image comprises a first periodic visual signal selected from the group consisting of: an image that changes intensity, an image that changes color, an image that changes pattern, and combinations thereof.

According to various aspects there is provided a method for presenting therapeutic light and sound on a computing device that includes a display screen and speaker. The method comprises presenting on the display screen a visual display comprising first and second images, and presenting on the speaker an audio composition comprising first and second audio streams. The first image is presented in a first portion of the visual display. The second image is presented in a second portion of the visual display forming a frame surrounding the perimeter of the first portion of the visual display, the frame having a uniform width that is about ½ the width of first portion. The first audio stream comprises a musical composition. The second audio stream includes a periodic audio signal comprising a series of clicks. The first image is selected from the group consisting of: a graphic image, a sequence of graphic images, a video image, and an interactive video image. The second image comprises a periodic visual signal selected from the group consisting of: an image that changes intensity, an image that changes color, an image that changes pattern, and combinations thereof. The changes of the periodic visual signal and the periodic audio signal have the same periodicity and are presented synchronously.

A device for presenting therapeutic light and sound, comprises: a processor, a display screen coupled to the processor, a speaker coupled to the processor, and a computer readable medium coupled to the processor. A first image is stored on the computer readable medium, the first image selected from the group consisting of: a graphic image, a sequence of graphic images, a video image, and an interactive video image. A second image stored on the computer readable medium, the second image comprising a periodic visual signal selected from the group consisting of: an image that changes intensity, an image that changes color, an image that changes pattern, and combinations thereof, where the changes in the periodic visual signal have a first periodicity. An audio composition is stored on the computer readable medium, the audio composition including a periodic audio signal comprising a series of clicks having a second periodicity that is the same as the first periodicity. The processor directs the display screen to present a visual display comprising the first image in a first portion of the visual display, and the second image in a second portion of the visual display that is positioned at the perimeter of the first portion. The processor further directs the speaker to present the audio composition with the periodic audio signal synchronous with the periodic visual signal.

Numerous benefits are achieved by way of the various embodiments over conventional techniques. For example, the various embodiments provide light and sound in a mobile application that can provide a therapeutic effect for people suffering from dementia or Alzheimer's disease. The light may be embedded in various repeating images and the sound may be embedded in specially composed music. In some embodiments, facial recognition may be used to ensure that the targeted person is using the application. These and other embodiments along with many of its advantages and features are described in more detail in conjunction with the text below and attached figures.

BRIEF DESCRIPTION OF THE DRAWINGS

Aspects and features of the various embodiments will be more apparent by describing examples with reference to the accompanying drawings, in which.

DETAILED DESCRIPTION

While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

Brain waves are generated when large groups of neurons oscillate on and off together. Neurons encode thoughts and actions and senses in these oscillations. Gamma brain waves are thought to help connect and process information throughout the brain. Providing the brain with light flashing at 40 hertz and sound reproduced at 40 hertz can cause the brain to generate gamma waves, which are diminished in Alzheimer's disease, at a corresponding 40 hertz.

Figure 1A:
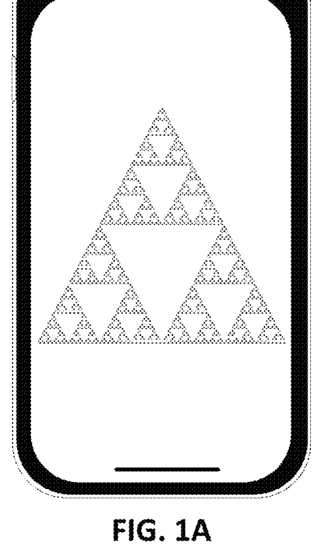
FIGS. 1A-1C are diagrams illustrating examples of fractal patterns displayed on a display of a mobile device according to various aspects of the present disclosure.
Figure 1B:
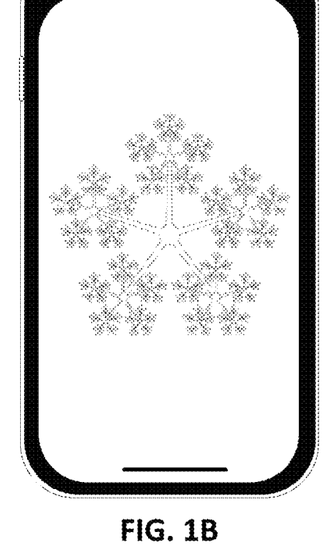
Figure 1C:
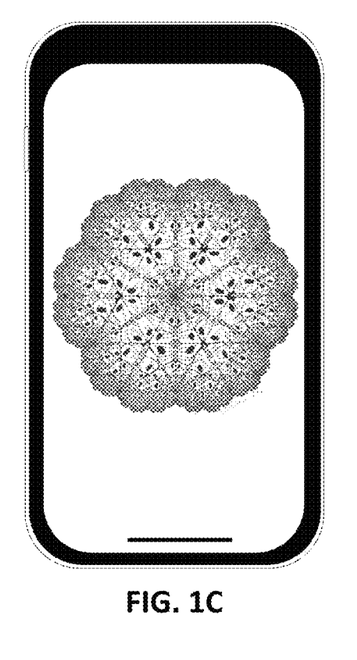

FIGS. 1A-1C are diagrams illustrating examples of fractal patterns displayed on a display of a mobile device according to various embodiments. As illustrated in FIGS. 1A-1C, the visual display may be presented on a display screen of a mobile phone, a display screen of a laptop computer, or a display screen of another mobile device. The visual display may present a fractal pattern, for example, but not limited to, the fractal patterns illustrated in FIGS. 1A-1C. According to aspects of the present disclosure, a user may select a fractal pattern to view via a user interface (not shown).

A fractal is a pattern that when seen as an image produces a picture which can be zoomed into infinity and will still produce the same picture. It can be cut into parts which look quite like a smaller version of the set that was started with. Examples of fractals in nature are snowflakes, tree branches, lightning, ferns, cacti, etc. According to aspects of the present disclosure, to produce a therapeutic effect the fractal pattern may change at a rate of approximately 40 times per second (e.g., 40 Hz). Once a fractal pattern is selected, the pattern may be displayed at the 40 Hz rate for a specified duration. The duration may be specified by a user or may be a preset duration.

The selected fractal pattern may perceptibly change intensity at the 40 Hz rate. The fractal pattern may be a single image that changes intensity or may be a changing image of the fractal pattern that also changes at the 40 Hz rate. Alternatively or additionally, the image may change color at the 40 Hz rate.

An audio composition may be presented together with the displayed fractal pattern. The audio composition may include an audible 40 Hz tone. The audible 40 Hz tone may be presented in synchronization with the 40 Hz rate of change of the fractal pattern. The audio composition may be specifically composed to include the 40 Hz tone as an element of the musical composition. When included in a specifically composed composition, the 40 Hz tone, while audible, may blend with the music of the audio composition. Alternatively, a 40 Hz tone may be embedded in a piece of music not specifically composed for the purpose. In such cases, the 40 Hz tone will be audible but may not be in harmony with the audio composition. A plurality of audio compositions may be available for selection by the user.

In order to ensure that a particular user is actually using the application, a facial recognition routine may be executed to identify the user. Upon the first use, the application may execute a user registration routine to request a user to be registered with the application. For example, a prompt may be displayed on the display of the computing device requesting a user to register with the application. The application may use the camera of the computing device to capture a facial image of the user.

In some implementations, the facial image of the user may be stored in memory of the computing device as a registered user. In some implementations, the facial image of the user may be stored in a remote server in communication with the computing device. In some implementations, portions of the facial image of the user may be stored in memory of the computing device and other portions of the facial image of the user may be stored in a remote server in communication with the computing device. In some implementations, identifying information such as name, date of birth, etc., may be requested. The identifying information may be associated with the facial image of the registered user and stored in memory of the computing device and/or the server.

The registered user may be issued a license for use of the application on the computing device. In some implementations, one or more users may be registered with the application. In such cases, the application may track use by each registered user individually. Individual licenses may be issued to the individual users. In some implementations, an entity such as a hospital or other health care facility may be issued a group license. In such cases, a caregiver in the institutional setting may track use of the application by individual users.

When execution of the application begins after one or more users have been registered with the application, the facial recognition routine may use the camera of the computing device to capture a facial image of the user. The facial recognition routine may then access the memory of the computing device and/or the remote server to determine if the facial image matches a facial image of a registered user. If the facial recognition routine determines that the facial image does not match a registered user, the application may request the user to register and may execute the registration routine.

If the facial recognition routine determines that the facial image matches a registered user, the application may continue execution by requesting the user to select a fractal pattern for viewing and an audio composition for listening. For example, the application may cause the display of the computing device to display a list of available fractal patterns for selection and may display a list of available audio compositions for selection. In some implementations, the elements in the lists may be displayed as icons. In some implementations, the fractal patterns and audio compositions may be selected by the application. The combination of a fractal pattern and an audio composition may also be referred to herein as a program.

A timer may be initiated when the program begin playing. The fractal pattern and audio composition may play for a duration set by the timer. In some implementations, the user may be prompted to set a duration for the timer. For example, the application may cause the display of the computing device to display a duration the user wishes to play the fractal pattern and audio composition. In some implementations, the duration may be set by the application.

The timer may track whether the user is in a proximity of the audio composition and/or visual display, and the amount of time a user actually spends using the application. For example, the facial recognition routine may be executed at preset intervals (e.g., every 30 seconds, one minute, two minutes, five minutes, or another interval) to capture a facial image of the user to determine that the user is engaged with the application. If the facial image is not captured or if the user stops execution of the application, the application records the time indicated by the timer, determines the duration that the user actually used the application, and stores the duration in memory associated with the registered user. The time and usage data for the user may be stored in a remote server. An administrative mode of the application may allow a third party, for example, a family member, medical professional, or other third-party, to access the stored time and usage data and determine the amount of time the registered user used the application.

Figure 2:
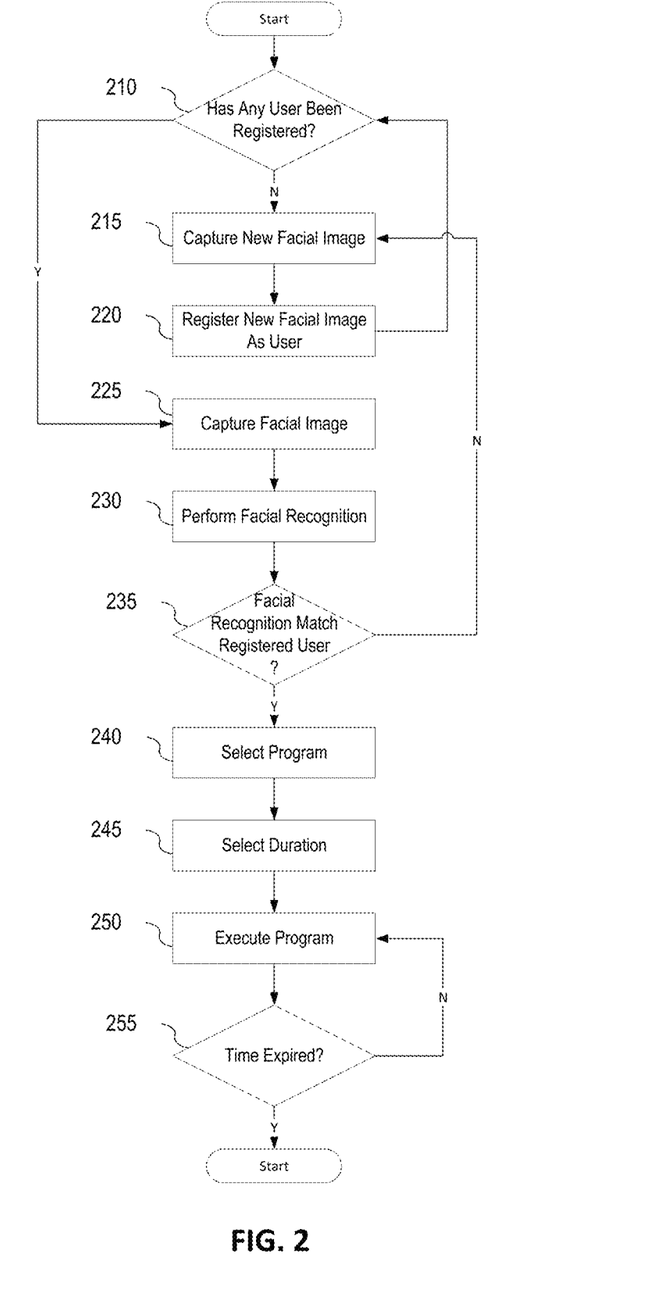
FIG. 2 is a flow chart illustrating an example of a method for executing an application for providing sound and light for producing therapeutic effects according to various aspects of the present disclosure.

FIG. 2 is a flowchart illustrating an example of a method 200 for executing an application for providing sound and light for producing therapeutic effects according to various aspects of the present disclosure. Block 210, it may be determined whether any user has been registered to use the application. Upon the first use of the application, a user should be registered in order to track the amount of time the user spends with the application. By registering a user with the application, the application can verify that the registered user is actually using the application.

In response to determining that no user has been registered to the application (210-N), at block 215, a new facial image of the user may be captured. A user registration routine may be executed. For example, a camera associated with the computing device may be used to capture a facial image of the user. The camera may be integrated into the computing device or may be externally coupled to the computing device. A facial recognition routine may be executed to generate facial recognition data of the user.

At block 220, the new facial image may be registered with the application. Facial recognition data may be stored in a memory of the computing device and/or a remote server and associated with the application as a registered user. Optionally, additional information associated with the user may be entered and stored in memory with the facial recognition data. In some implementations, a third party may perform the registration process with the user. In some implementations, the user may self-register. Upon completion of registration, the method may return to operation 210.

In response to determining that at least one user has been registered to the application (210-Y), at block 225, a facial image of the user may be captured using the camera associated with the computing device.

At block 230, facial recognition may be performed on the captured image. A facial recognition routine may be executed to generate facial recognition data of the user.

At block 235, it may be determined whether the user is a registered user. The facial recognition data may be compared to facial recognition data of registered users stored in the memory of the computing device and/or the remote server. The computing device may access the facial recognition data from its memory and/or from the remote server to perform the comparison. In response to determining that the facial recognition data of the user does not match facial recognition data of any registered user (235-N), the method may continue at block 215 to execute the user registration routine. Execution of the application may not advance past the user registration routine until a registered user is recognized.

In response to determining that the captured facial image matches the facial image of a registered user (235-Y), at block 240 the user may be prompted to select a program. For example, the user may be prompted to select a fractal pattern for viewing and a musical composition for listening. In some implementations, the program may be selected by the application.

At block 245, the user may be prompted to select a duration for using the program. For example, the user may be provided with predetermined times (e.g., 30 minutes, one hour, etc.) or may select a custom duration for using the program. In some implementations, the duration may be selected by the application.

At block 250, the application may execute the program. A timer may be initiated to time the duration of the program and the application may cause the fractal pattern to be displayed and the audio composition to be played. The timer may also time a specified duration for periodically executing the facial recognition routine.

At block 255, it may be determined whether the specified duration for executing the program has expired. In response to determining that the duration has not expired (255-N), program execution may continue at block 250. The facial recognition routine may be executed periodically to determine that the registered user is viewing/listening to the application. In response to determining that the specified duration has expired (255-Y), the method may end.

The timer may track the duration a user actually spends using the application. For example, the facial recognition routine may be executed at preset intervals (e.g., every 30 seconds, one minute, or another interval) to capture a facial image of the user to determine that the user is engaged with the application. If the facial image is not captured or if the user stops execution of the application, the application records the time indicated by the timer, determines the duration that the user actually used the application, and stores the duration in memory associated with the registered user.

The specific operations illustrated in FIG. 200 provide a particular method for executing an application for providing sound and light for producing therapeutic effects according to an embodiment of the present disclosure. Other sequences of operations may also be performed according to alternative embodiments. For example, alternative embodiments of the present disclosure may perform the operations outlined above in a different order. Moreover, the individual operations illustrated in FIG. 200 may include multiple sub-operations that may be performed in various sequences as appropriate to the individual operation. Furthermore, additional operations may be added or removed depending on the particular applications.

The method 200 may be embodied on a non-transitory computer readable medium, for example, but not limited to, a memory or other non-transitory computer readable medium known to those of skill in the art, having stored therein a program including computer executable instructions for making a processor, computer, or other programmable device execute the operations of the method.

Figure 3:
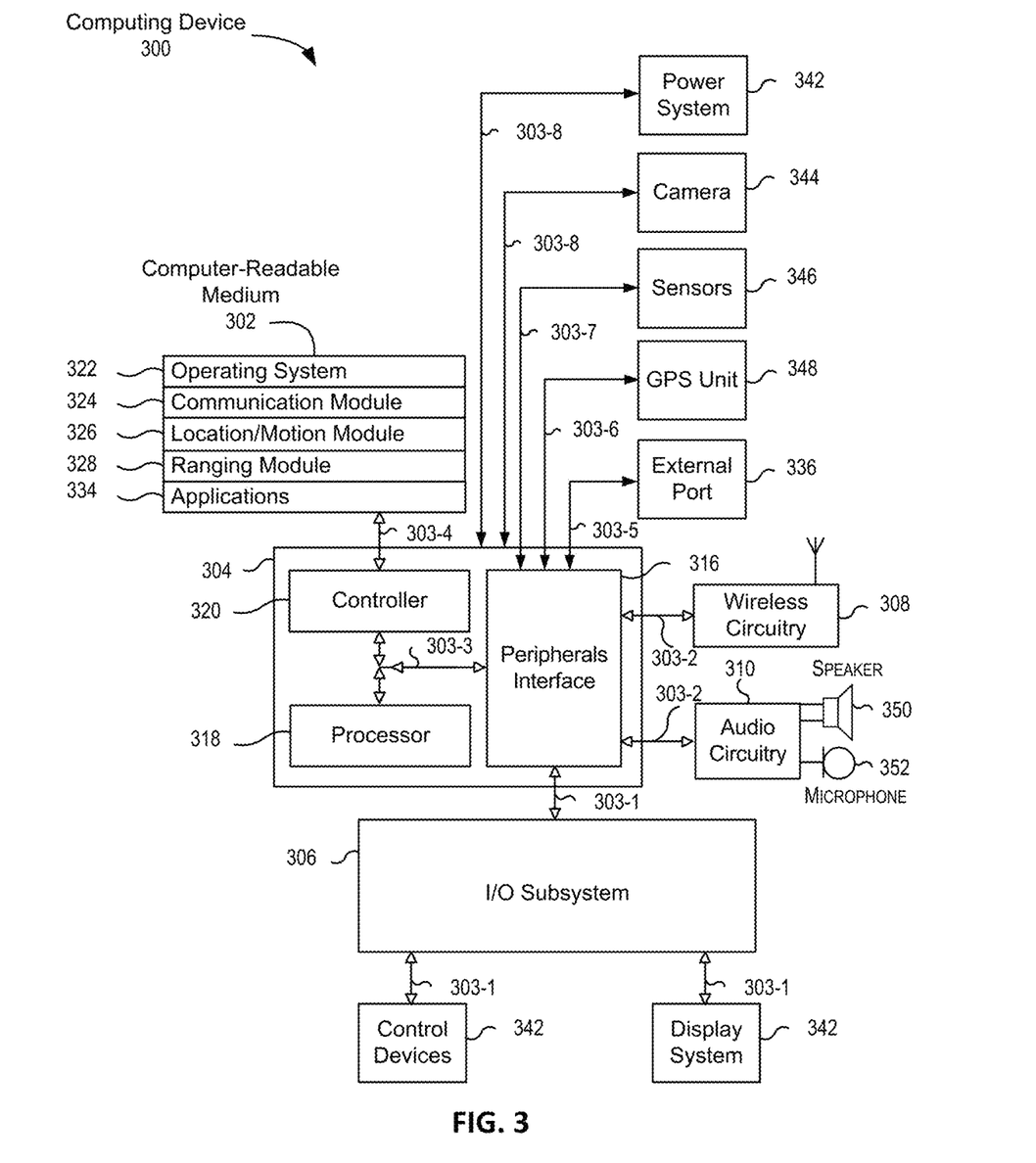
FIG. 3 is a block diagram of an example of a computing device according to various aspects of the present disclosure.

FIG. 3 is a block diagram of an example of a computing device 300 according to various aspects of the present disclosure. Computing device 300 generally includes computer-readable medium 302, a processing system 304, an Input/Output (I/O) subsystem 306, wireless circuitry 308, and audio circuitry 310 including speaker 312 and microphone 314. These components may be coupled by one or more communication buses or signal lines 303. Computing device 300 can be any portable electronic device, including a handheld computer, a tablet computer, a mobile phone, laptop computer, tablet device, media player, personal digital assistant (PDA), a multi-function device, a portable gaming device, a headset, or the like, including a combination of two or more of these items. Alternatively, computing device 300 may also comprise or be coupled to non-portable components, such as a large screen display and bookshelf or standing audio monitors or speakers.

In a preferred embodiment, computing device 300 does not comprise a separate video display, speaker, headset, or other separate accessory, but is a self-contained audiovisual display such as a mobile phone, tablet, gaming device, or other handheld mobile device. Dementia-afflicted subjects may be hesitant to disclose or seek assistance for their condition. Dementia can also be associated with delusions and paranoia, which may exacerbate the subject's desire to conceal their condition. These symptoms of avoidance can lead to social isolation, overdependence on family, or otherwise decrease the subject's quality of life. Therefore, it is desirable to provide a therapeutic treatment that is easily accessible to the subject, such as a simple application that is readily downloadable to a handheld device without the need for a previous diagnosis or prescription, and that may be used on the device without requiring an external accessory.

It should be apparent that the architecture shown in FIG. 3 is only one example of an architecture for device 300, and that device 300 can have more or fewer components than shown, or a different configuration of components. The various components shown in FIG. 3 can be implemented in hardware, software, or a combination of both hardware and software, including one or more signal processing and/or application specific integrated circuits.

Wireless circuitry 308 is used to send and receive information over a wireless link or network to one or more other devices' conventional circuitry such as an antenna system, an RF transceiver, one or more amplifiers, a tuner, one or more oscillators, a digital signal processor, a CODEC chipset, memory, etc. Wireless circuitry 308 can use various protocols, e.g., as described herein. In various embodiments, wireless circuitry 308 is capable of establishing and maintaining communications with other devices using one or more communication protocols, including time division multiple access (TDMA), code division multiple access (CDMA), global system for mobile communications (GSM), Enhanced Data GSM Environment (EDGE), wideband code division multiple access (W-CDMA), Long Term Evolution (LTE), LTE-Advanced, WiFi (such as IEEE 802.11a, IEEE 802.11b, IEEE 802.11g and/or IEEE 802.11n), Bluetooth, Wi-MAX, voice over Internet Protocol (VOIP), near field communication protocol (NFC), a protocol for email, instant messaging, and/or a short message service (SMS), or any other suitable communication protocol, including communication protocols not yet developed as of the filing date of this document.

Wireless circuitry 308 is coupled to processing system 304 via peripherals interface 316. Peripherals interface 316 can include conventional components for establishing and maintaining communication between peripherals and processing system 304. Voice and data information received by wireless circuitry 308 (e.g., in speech recognition or voice command applications) is sent to one or more processors 318 via peripherals interface 316. One or more processors 318 are configurable to process various data formats for one or more application programs 334 stored on medium 302.

Peripherals interface 316 couple the input and output peripherals of device 300 to the one or more processors 318 and computer-readable medium 302. One or more processors 318 communicate with computer-readable medium 302 via a controller 320. Computer-readable medium 302 can be any device or medium that can store code and/or data for use by one or more processors 318. Computer-readable medium 302 can include a memory hierarchy, including cache, main memory and secondary memory. The memory hierarchy can be implemented using any combination of RAM (e.g., SRAM, DRAM, DDRAM), ROM, FLASH, magnetic and/or optical storage devices, such as disk drives, magnetic tape, CDs (compact disks) and DVDs (digital video discs). In some embodiments, peripherals interface 316, one or more processors 318, and controller 320 can be implemented on a single chip, such as processing system 304. In some other embodiments, they can be implemented on separate chips.

Processor(s) 318 can include hardware and/or software elements that perform one or more processing functions, such as mathematical operations, logical operations, data manipulation operations, data transfer operations, controlling the reception of user input, controlling output of information to users, or the like. Processor(s) 318 can be embodied as one or more hardware processors, microprocessors, microcontrollers, field programmable gate arrays (FPGAs), application-specified integrated circuits (ASICs), or the like.

Device 300 also includes a power system 342 for powering the various hardware components. Power system 342 can include a power management system, one or more power sources (e.g., battery, alternating current (AC)), a recharging system, a power failure detection circuit, a power converter or inverter, a power status indicator (e.g., a light emitting diode (LED)) and any other components typically associated with the generation, management and distribution of power in mobile devices.

The computing device 300 can include a camera 344. In some embodiments, device 300 includes sensors 346. Sensors can include accelerometers, compass, gyrometer, pressure sensors, audio sensors, light sensors, barometers, and the like. Sensors 346 can be used to sense location aspects, such as auditory or light signatures of a location.

In some embodiments, computing device 300 can include a GPS receiver, sometimes referred to as a GPS unit 348. A mobile device can use a satellite navigation system, such as the Global Positioning System (GPS), to obtain position information, timing information, altitude, or other navigation information. During operation, the GPS unit can receive signals from GPS satellites orbiting the Earth. The GPS unit analyzes the signals to make a transit time and distance estimation. The GPS unit can determine the current position (current location) of the mobile device. Based on these estimations, the mobile device can determine a location fix, altitude, and/or current speed. A location fix can be geographical coordinates such as latitudinal and longitudinal information.

One or more processors 318 run various software components stored in medium 302 to perform various functions for device 300. In some embodiments, the software components include an operating system 322, a communication module 324 (or set of instructions), a location module 326 (or set of instructions), a ranging module 328, and other application programs 334 (or set of instructions).

Operating system 322 can be any suitable operating system, including iOS, Mac OS, Darwin, RTXC, LINUX, UNIX, OS X, WINDOWS, or an embedded operating system such as VxWorks. The operating system can include various procedures, sets of instructions, software components and/or drivers for controlling and managing general system tasks (e.g., memory management, storage device control, power management, etc.) and facilitates communication between various hardware and software components.

Communication module 324 facilitates communication with other devices over one or more external ports 336 or via wireless circuitry 308 and includes various software components for handling data received from wireless circuitry 308 and/or external port 336. External port 336 (e.g., USB, FireWire, Lightning connector, 60-pin connector, etc.) is adapted for coupling directly to other devices or indirectly over a network (e.g., the Internet, wireless LAN, etc.).

Location/motion module 326 can assist in determining the current position (e.g., coordinates or other geographic location identifiers) and motion of device 1300. Modern positioning systems include satellite-based positioning systems, such as Global Positioning System (GPS), cellular network positioning based on "cell IDs," and Wi-Fi positioning technology based on a Wi-Fi networks. GPS also relies on the visibility of multiple satellites to determine a position estimate, which may not be visible (or have weak signals) indoors or in "urban canyons." In some embodiments, location/motion module 326 receives data from GPS unit 348 and analyzes the signals to determine the current position of the mobile device. In some embodiments, location/motion module 326 can determine a current location using Wi-Fi or cellular location technology. For example, the location of the mobile device can be estimated using knowledge of nearby cell sites and/or Wi-Fi access points with knowledge also of their locations. Information identifying the Wi-Fi or cellular transmitter is received at wireless circuitry 308 and is passed to location/motion module 326. In some embodiments, the location module receives the one or more transmitter IDs. In some embodiments, a sequence of transmitter IDs can be compared with a reference database (e.g., Cell ID database, Wi-Fi reference database) that maps or correlates the transmitter IDs to position coordinates of corresponding transmitters, and computes estimated position coordinates for device 300 based on the position coordinates of the corresponding transmitters. Regardless of the specific location technology used, location/motion module 326 receives information from which a location fix can be derived, interprets that information, and returns location information, such as geographic coordinates, latitude/longitude, or other location fix data.

Ranging module 328 can send/receive ranging messages to/from an antenna, e.g., connected to wireless circuitry 308. The messages can be used for various purposes, e.g., to identify a sending antenna of a device, determine timestamps of messages to determine a distance of mobile device 300 from another device. Ranging module 328 can exist on various processors of the device, e.g., an always-on processor (AOP), a UWB chip, and/or an application processor. For example, parts of ranging module 328 can determine a distance on an AOP, and another part of the ranging module can interact with a sharing module, e.g., to display a position of the other device on a screen in order for a user to select the other device to share a data item. Ranging module 328 can also interact with a reminder module that can provide an alert based on a distance from another mobile device.

The one or more applications 334 on device 300 can include any applications installed on the device 300, including without limitation, the light and sound applications, facial recognition and registration routines described herein, a browser, address book, contact list, email, instant messaging, social networking, word processing, keyboard emulation, widgets, JAVA-enabled applications, encryption, digital rights management, voice recognition, voice replication, a music player (which plays back recorded music stored in one or more files, such as MP3 or AAC files), etc.

There may be other modules or sets of instructions (not shown), such as a graphics module, a time module, etc. For example, the graphics module can include various conventional software components for rendering, animating and displaying graphical objects (including without limitation text, web pages, icons, digital images, animations and the like) on a display surface. In another example, a timer module can be a software timer. The timer module can also be implemented in hardware. The time module can maintain various timers for any number of events.

I/O subsystem 306 can be coupled to a display system 342, which can be a touch-sensitive display. The display system displays visual output to the user in a GUI. The visual output can include text, graphics, video, and any combination thereof. Some or all of the visual output can correspond to user-interface objects. The display system can use LED (light emitting diode), LCD (liquid crystal display) technology, or LPD (light emitting polymer display) technology, although other display technologies can be used in other embodiments.

In some embodiments, I/O subsystem 306 can include user input devices such as a keyboard, mouse, and/or trackpad. The touch-sensitive display can also accept input from the user based at least part on haptic and/or tactile contact. In some embodiments, the touch-sensitive display forms a touch-sensitive surface that accepts user input. The touch-sensitive display/surface (along with any associated modules and/or sets of instructions in computer-readable medium 302) detects contact (and any movement or release of the contact) on the touch-sensitive display and converts the detected contact into interaction with user-interface objects, such as one or more soft keys, that are displayed on the touch screen when the contact occurs. In some embodiments, a point of contact between the touch-sensitive display and the user corresponds to one or more digits of the user. The user can make contact with the touch-sensitive display using any suitable object or appendage, such as a stylus, pen, finger, and so forth. A touch-sensitive display surface can detect contact and any movement or release thereof using any suitable touch sensitivity technologies, including capacitive, resistive, infrared, and surface acoustic wave technologies, as well as other proximity sensor arrays or other elements for determining one or more points of contact with the touch-sensitive display.

Further, I/O subsystem 306 can be coupled to one or more other physical control devices 342, such as pushbuttons, keys, switches, rocker buttons, dials, slider switches, sticks, LEDs, etc., for controlling or performing various functions, such as power control, speaker volume control, ring tone loudness, keyboard input, scrolling, hold, menu, screen lock, clearing and ending communications and the like. In some embodiments, in addition to the touch screen, device 300 can include a touchpad (not shown) for activating or deactivating particular functions. In some embodiments, the touchpad is a touch-sensitive area of the device that, unlike the touch screen, does not display visual output. The touchpad can be a touch-sensitive surface that is separate from the touch-sensitive display or an extension of the touch-sensitive surface formed by the touch-sensitive display.

In some embodiments, some or all of the operations described herein can be performed using an application executing on the user's device. Circuits, logic modules, processors, and/or other components may be configured to perform various operations described herein. Those skilled in the art will appreciate that, depending on implementation, such configuration can be accomplished through design, setup, interconnection, and/or programming of the particular components and that, again depending on implementation, a configured component might or might not be reconfigurable for a different operation. For example, a programmable processor can be configured by providing suitable executable code; a dedicated logic circuit can be configured by suitably connecting logic gates and other circuit elements; and so on.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium, such as a compact disk (CD) or DVD (digital versatile disk), flash memory, and the like. The computer readable medium may be any combination of such storage or transmission devices.

Computer programs incorporating various features of the present disclosure may be encoded on various computer readable storage media; suitable media include magnetic disk or tape, optical storage media, such as compact disk (CD) or DVD (digital versatile disk), flash memory, and the like. Computer readable storage media encoded with the program code may be packaged with a compatible device or provided separately from other devices. In addition, program code may be encoded and transmitted via wired optical, and/or wireless networks conforming to a variety of protocols, including the Internet, thereby allowing distribution, e.g., via Internet download. Any such computer readable medium may reside on or within a single computer product (e.g. a solid-state drive, a hard drive, a CD, or an entire computer system), and may be present on or within different computer products within a system or network. A computer system may include a monitor, printer, or other suitable display for providing any of the results mentioned herein to a user.

Figure 4:
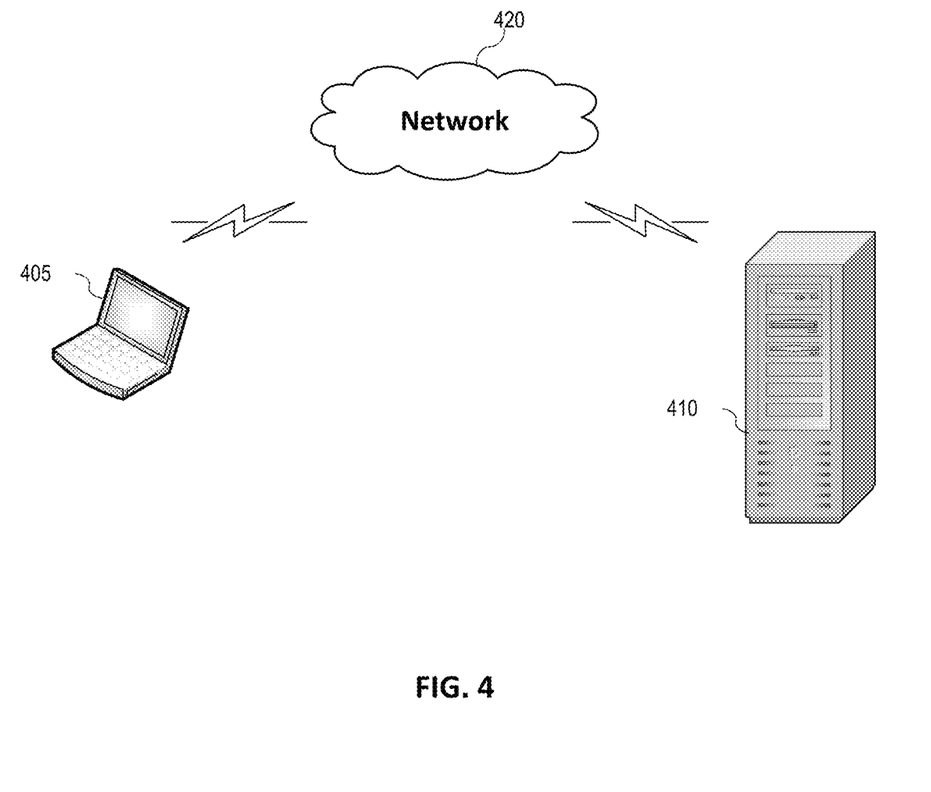
FIG. 4 is a block diagram of an example computing environment with an example computing device and server according to various aspects of the present disclosure.

FIG. 4 is a block diagram of an example computing environment 400 with an example computing device 405 and server 410 suitable for use in some example implementations. In accordance with aspects of the present disclosure, the computing device 405 and/or the server 410 may be configured substantially similar to the computing device 300.

Examples of the computing device 405 may include, but are not limited to, mobile devices (e.g., tablets, notebooks, laptops, personal computers, portable televisions, radios, and the like), and devices not designed for mobility (e.g., desktop computers, other computers, and the like). Any connected computing device may be functioning as, providing services of, or referred to as a server 410.

The computing device 405 and the server 410 may communicate via a network 420. In some implementations, the network 420 may be a wireless network, for example, but not limited to, a WiFi network. In some implementations, the network 420 may be wired network, for example, but not limited to, an Ethernet network.

Figure 5:
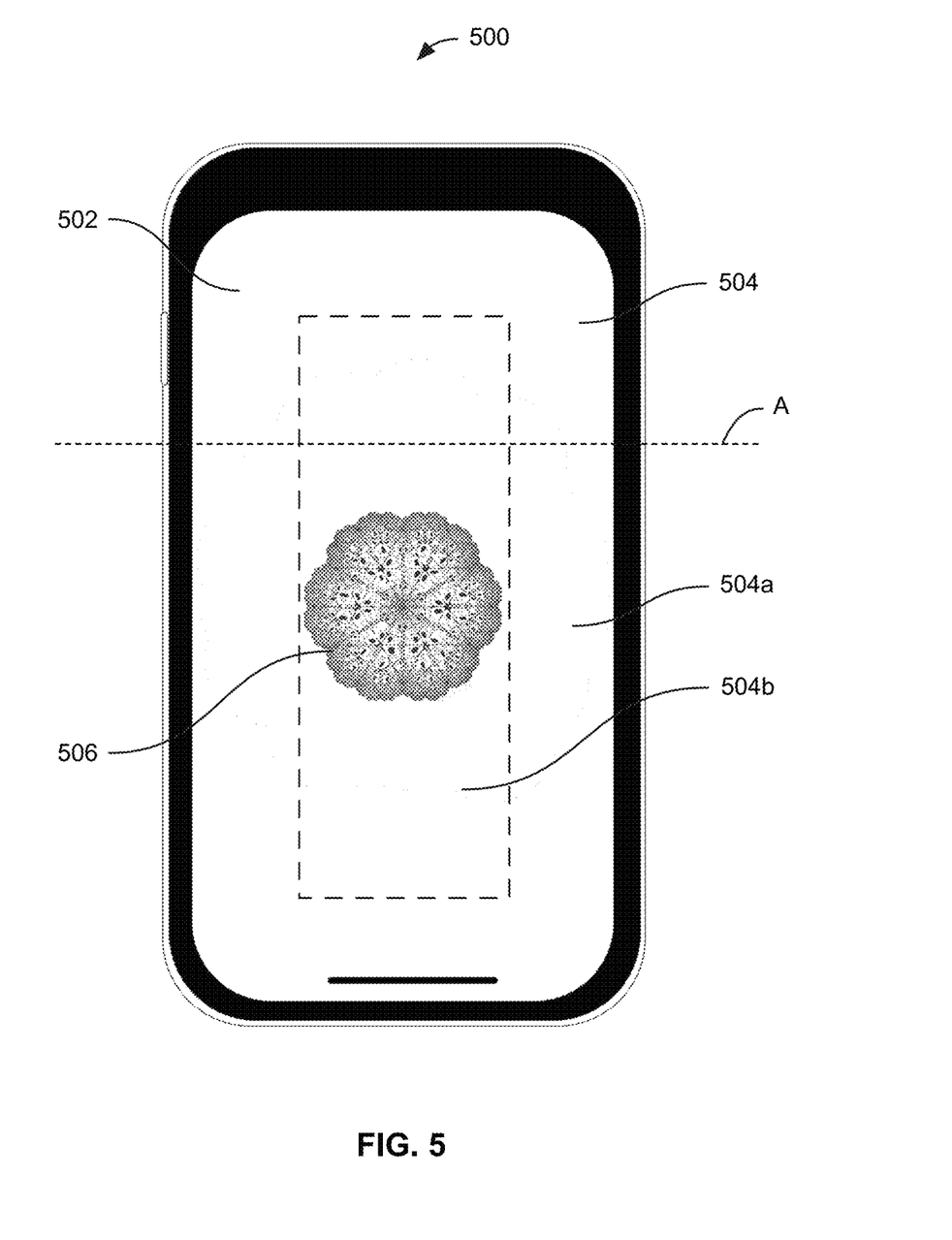
FIG. 5 is a diagram illustrating and alternative example of a fractal pattern displayed on a display of a mobile device according to various aspects of the present disclosure.

FIG. 5 shows an example of a computing device 300 (or 405) with a display system 342, such as a mobile device 500 that includes a display screen 502 for providing a sensory stimulus such as a display visual output 504. Visual output 504 includes a first or primary image for capturing the attention of the user, and a second image comprising a visual stimulus for promoting the generation of gamma brain waves. The primary image is designed to promote the user's engagement with visual output 504, and may be any visual display that is designed to entertain or otherwise appeal to the user. The primary image may, but need not be composed for the purpose of providing a visual stimulus. Suitable primary images include a graphic image, series or sequence of graphic images such as a fractal pattern 506, a video image (e.g., movie, television show), or interactive video image (e.g., video game). Video images are particularly useful to encourage the user's continuous and repeated engagement with visual output 504.

The visual stimulus comprises a periodic visual signal or series of visual events, such as a visual display that changes intensity (e.g., flashing light), changes color, and/or changes pattern (e.g., a series of fractal patterns). In one embodiment, the changes of the visual stimulus have a periodicity of 40 times per second (40 Hz). The visual stimulus may be a separate from the primary image and/or may be incorporated in the primary image.

In one embodiment, visual display 504 comprises a first portion 504a, and a second portion 504b that is positioned at an outer border of visual display portion 504a. In a preferred embodiment, visual display portion 504b forms a frame that surrounds central visual display portion 504a. Frame 504b preferably has a uniform width around the perimeter of visual display portion 504a. The dimensions of the second portion 504b are preferably sufficient to ensure that the visual stimulus captures the user's attention, whether conscious or not. In one embodiment, frame 504b has a uniform width that is about ½ or less than the width or shortest dimension of visual display portion 504a, and alternatively about ¹⁄₁₀ or less. In another embodiment, ratio of the width of the first portion to the width of the second portion is about 1:1 or less, and alternatively about 1:5 or less—e.g., along a line "A" through visual display 504 that defines the shortest dimension of the first portion.

In one embodiment, visual display portion 504a comprises a primary image, and visual display portion 504b comprises a visual stimulus. For example, visual display portion 504a may show a fractal image 506, and visual display portion 504b may show a flashing light. In one embodiment, visual display portion 504a also incorporates a visual stimulus. For example, visual display portion 504a may comprise a series of fractal images 506 that change with a periodicity of 40 Hz. In a preferred embodiment, the visual stimulus of visual display portions 504a and 504b have the same periodicity, and more preferably are synchronized—e.g., the changing fractal images 506 and the flashing light have a periodicity 40 Hz and are synchronized.

In one embodiment, the sensory stimulus comprises an audio stimulus. For example, mobile device 500 may include a speaker (e.g., speaker 312) for presenting an audio composition that comprises a first or primary audio stream for capturing the attention of the user and/or a second audio stream comprising an audio stimulus for promoting the generation of gamma brain waves. The primary audio stream may be related to the primary image, and is typically not composed for the purpose of providing an audio stimulus. For example, the primary audio stream may be a musical composition that reflects the subject matter of a graphic image or series of graphic images comprising the primary image. Alternatively, the primary audio stream may be the audio track for a primary image movie, television show, or video game, or may be otherwise be designed to promote the theme of the primary image.

The audio stimulus comprises a periodic audio signal or series of audio events, such as a series of pulses or bursts of sound (e.g., clicks). The periodicity of the audio stimulus is preferably synchronized with the periodicity of the visual stimulus. In one embodiment, the audio stimulus comprises a series of clicks with a periodicity of 40 Hz (i.e. 40 clicks per second). The pulses of sound may be monaural or binaural, and may vary in tone or may have a constant tone (e.g., a tone having frequency of 40 Hz). In addition to the pulses of sound, the audio stimulus may also comprise a constant tone, such as a tone produced by a tuning fork having a frequency of 40 Hz. Where the audio composition comprises both a primary audio stream and an audio stimulus, the audio stimulus may be blended into the primary audio stream (e.g., a 40 Hz tone) and/or may comprise a separate element from the primary audio stream (e.g., clicks not in harmony with the primary audio stream).

Those of skill in the art will appreciate that a primary audio stream comprising a musical composition, or the audio track to a movie, television show, or video game will vary in volume. In one embodiment, the volume of the audio stimulus will also vary to ensure that it can be continuously heard by the user, and does not drown out or become overwhelmed by the primary audio stream. In a preferred embodiment, the volume of the audio stimulus is automatically adjusted such that the ratio of the volume of the primary audio stream to the volume of the audio stimulus is approximately constant.

In one embodiment, the audio composition comprises a primary audio stream that is produced by a musical instrument. The musical instrument is preferably adapted to generate low frequency tones that are believed to be particularly beneficial for sound healing. In one embodiment, the musical instrument is an acoustic-electronic musical instrument that comprises one or more acoustic elements, such as a stringed instrument (e.g., that may be bowed or plucked), a standing bell (e.g., that may be struck or rubbed), and/or tuning forks, and one or more electronic elements, such as an electronic keyboard and/or instrument/sound effects synthesizer. The acoustic elements may be provided with or without electronic amplification. An example of a suitable acoustic-electronic musical instrument is described in U.S. Pat. Nos. 9,685,149 and 10,068,560 to Quittner, which are incorporated herein by reference.

In one embodiment, the primary audio stream is composed to generally entertain or otherwise engage the subject. For example, the primary audio stream may comprise modulation effects (e.g., frequency, phase and/or amplitude modulation) that produce a complex pattern of wavy/wobble sounds that subjects may find calming. Acoustic-electronic musical instruments are particularly suitable for creating such audio content. The sound of standing bells (e.g., crystal bowls, or Tibetan metal singing bowls) are thought to be healing. These therapeutic sounds may be complemented by bowed or plucked strings that produce deep reverberant sounds which attract the attention of the subject. The primary audio stream is preferably designed complement or reinforce the audio stimulus. For example, the primary audio stream may comprise a wavy repetitive pattern with a periodicity that is a multiple of the periodicity of the audio stimulus.

In one embodiment, mobile device 500 is configured to display a visual output 504 and play an audio composition. Visual output 504 includes a primary image in a central visual display portion 504a that comprises a series of fractal patterns that change color, and a visual stimulus in a visual display portion 504b forming a frame surrounding visual display portion 504a that comprises a flashing light. The primary image changes color and pattern, and the visual stimulus flashes with a periodicity of 40 Hz, and are synchronized. The audio composition includes a primary audio stream produced by an acoustic-electronic musical instrument, and an audio stimulus that comprises repeated clicks with a periodicity of 40 Hz. The periodicity of the flashing light and clicks (and frequency of the tone) are synchronized.

In one embodiment, visual output 504 and the audio composition are stored on computer readable medium 302. Processors 318 run an application program that controls display system 342 and display screen 502 to provide display visual output 504, and controls speaker 312 to provide the audio composition.

Treatment with sensory (visual and/or audio) stimulus is preferably an exposure period of at least about 5 seconds to about 1 hour or more. A few minutes of exposure to visual and audio stimulus has been shown to increase EEG power and coherence. Audio stimulus of as little as 5 seconds has been shown to modulate EEG power and phase synchronization, and activation of frontal, temporal and central regions of the brain has been found within 15 minutes. Studies of subjects with early-stage Alzheimers suggest that exposure to visual and audio stimulus for an hour per day may slow the progression of brain atrophy, and improve brain function. Visual stimulus for a period of 1 hour per day has also been shown to reduce neuronal degradation in mouse models of Alzheimer's.

In one embodiment, the computing device (e.g., mobile device 500) is configured to provide or present a visual and/or audio stimulus for an exposure period of about 5 seconds to about 1 hour or more, such as, for example, about 5, 10, 15, 20, 25, or 30 seconds, or about 1, 2, 3, 4, 5, 6, 7, 8, 9, 10, 11, 12, 13, 14, 15, 20, 25, 30, 40, 50, or 60 minutes. For some subjects, exposure periods of longer than about 1 hours may create repetition fatigue and discourage treatment. The visual display or audio composition may comprise a short segment that is repeated or looped during the period of exposure to sensory stimulus. In one embodiment the segment has a length or duration of 5, 10, or 15 minutes, and is repeated over the treatment period—e.g., 12, 6, or 4 times in an exposure period of an hour. Alternatively, the visual display or audio composition may be non-repeating and have a fixed length corresponding to the treatment period.

In one embodiment, the computing device tracks the amount of time the user is in the proximity of or otherwise engaged with the visual display and/or audio composition, to promote exposure to the sensory stimulus for the appropriate amount of time. For example, the computing device may include a timer and a facial recognition system with a facial recognition routine as described above, that detects or determines whether the user is, or is not engaged with the visual display and/or audio composition. In one embodiment, a timer is set with a predetermined time period for exposure to the sensory stimulus, and the timer is initiated when the visual display and/or audio composition begins playing. Once the timer reaches the predetermined time period, the computing device may stop play of the visual display and/or audio composition. The computing device may pause the timer during periods where the user is not engaged, and may either recontinue or restart the timer when the user reengages. Play of the visual display and audio composition may be paused during periods where the user is not engaged, or may simply continue as appropriate. For example, a non-repeating visual display and audio composition having a fixed length may be paused and recontinued (or restarted). Alternatively, a visual display and audio composition comprising a looped segment may simply continue playing until the timer stops.

The computing device may also track the user's daily exposure to the sensory stimulus. In one embodiment, the computing device stores or is programmed with a sequence of predetermined time periods. For example, the computing device may be programmed to increase the user's exposure to sensory stimulus over time, such as a sequence that increases incrementally each week (or 7 exposures). In one embodiment, the sequence of predetermined time periods begins with an exposure of 5 seconds per day, and increases each week in 5-minute increments to a maximum exposure of 1 hour per day.

The examples and embodiments described herein are for illustrative purposes only. Various modifications or changes in light thereof will be apparent to persons skilled in the art. These are to be included within the spirit and purview of this application, and the scope of the appended claims, which follow.

What is claimed is:

1. A computer-implemented method of presenting a picture and a sound on an electronic device having a housing and a camera, an electronic display screen, and a speaker housed within the housing, comprising the steps of:

presenting on the display screen a visual display comprising first animated sequence of images and a second animated sequence of images, the first animated sequence of images being presented in a first portion of the visual display, and the second animated sequence of images being presented in a second portion of the visual display arranged about at least part of a perimeter of the first portion, the second portion occupying at least 30% of a total viewable area of the visual display, wherein the second animated sequence of images includes at least a first image and a second image that is visually distinct from the first image;

detecting using the camera a facial image of a user of the electronic device;

tracking a time duration during which or an instance in which the user is facing the display screen;

storing in an electronic storage medium a calculation or a value indicative of how long or whether the user was facing the visual display;

simultaneously, while presenting the visual display on the display screen and responsive to the user being determined to be facing the visual display, causing to be played through the speaker an audio composition that includes a periodic audio signal having a periodicity in a range of 30-50 times per second by playing repeatedly through the speaker at the periodicity at least a first sound level followed by either no sound or a second sound level distinct from the first sound level;

the second animated sequence of images alternating at the periodicity between at least the first image and the second image;

wherein the periodic audio signal is synchronized with the second animated sequence of images such that the first image is presented repeatedly in the second portion relative to the display screen and the first sound level is played through the speaker simultaneously with the presentation of the first image on the display screen;

wherein the first animated sequence includes a graphic image, a sequence of graphic images, a video image, or an interactive video image; and wherein the second image includes an image that changes intensity, an image that changes color, an image that changes pattern, and combinations thereof.

2. The method of claim 1, wherein the first animated sequence includes an animation in which elements of the animation are displayed to appear as converging toward a center of the first portion or as moving away from the center of the first portion or following an undulating pattern in which some elements are displayed to appear as converging toward the center while other elements are displayed to appear as moving away from the center of the first portion, or vice versa.

3. The method of claim 2, wherein the elements form a multi-color kaleidoscopic or fractal pattern, and wherein a level or volume of the periodic audio signal is adjusted based on a configuration of the pattern without changing the periodicity of the periodic audio signal being played through the speaker and without changing the periodicity of the second animated sequence of images being displayed in the second portion of the display screen.

4. The method of claim 1, further comprising responsive to detecting that the user is not facing the display screen, displaying an alert indicating that the user is no longer facing the display screen or communicating to an external system remote from the electronic device a signal indicating that the user is no longer facing the display screen.

5. The method of claim 1, further comprising playing through the speaker a musical composition simultaneously with the periodic audio signal while simultaneously displaying the second animated sequence of images in the second portion of the display screen, the musical composition being generated by a music machine, wherein the music machine is an acoustic-electronic musical instrument comprising:

a platform;

a plurality of stringed instruments disposed around a perimeter of the platform, the plurality of stringed instruments disposed in a substantially vertical orientation; and a central mast disposed substantially at a center of the platform, wherein each of the plurality of stringed instruments is strung with a musical instrument string, and wherein each musical instrument string is tuned to produce a musical tone when caused to vibrate.

* * * * *